United States Patent [19]

Albrecht et al.

[11] 4,105,775

[45] Aug. 8, 1978

[54] FUNGICIDAL DISPERSIONS OF 2-BENZIMIDAZOLE-METHYL-CARBAMATE

[75] Inventors: Konrad Albrecht, Fischbach, Taunus; Heinz Frensch, Frankfurt am Main; Kurt Hartel, Hofheim, Taunus, all of Fed. Rep. of Germany

[73] Assignee: Hoechst Aktiengesellschaft, Frankfurt am Main, Fed. Rep. of Germany

[21] Appl. No.: 786,497

[22] Filed: Apr. 11, 1977

Related U.S. Application Data

[63] Continuation of Ser. No. 634,658, Nov. 24, 1975, abandoned, which is a continuation of Ser. No. 519,040, Oct. 29, 1974, abandoned.

[30] Foreign Application Priority Data

Oct. 31, 1973 [DE] Fed. Rep. of Germany ....... 2354468

[51] Int. Cl.² ............................................. A01N 9/22
[52] U.S. Cl. ................................ 424/273 R; 424/365
[58] Field of Search ................................ 424/273, 365

[56] References Cited

U.S. PATENT DOCUMENTS

| 3,657,443 | 4/1972 | Klopping | 424/273 |
|---|---|---|---|
| 3,833,520 | 9/1974 | Tirpak et al. | 424/78 |
| 3,930,010 | 12/1975 | Klopping | 424/273 |

*Primary Examiner*—V. D. Turner
*Attorney, Agent, or Firm*—Curtis, Morris & Safford

[57] ABSTRACT

Stable dispersions having an improved systemic fungicidal activity are composed of about 5 to 30% by weight of 2-benzimidazole-methyl-carbamate, about 60 to 85% by weight of liquid esters of ($C_1 - C_{12}$) monoalcohols and ($C_2 - C_{10}$) carboxylic acids, about 2 to 10% by weight of a combination of a ($C_8 - C_{12}$)-monoalkylphenol polyglycol ether and castor oil polyglycol ether and about 0.1 to 5% by weight of Ca-($C_8-C_{15}$)-monoalkyl-benzene sulfonate.

2 Claims, No Drawings

FUNGICIDAL DISPERSIONS OF 2-BENZIMIDAZOLE-METHYL-CARBAMATE

This is a continuation of application Ser. No. 634,658, filed Nov. 24, 1975, which, in turn, is a continuation of application Ser. No. 519,040, filed Oct. 29, 1974, both of which are abandoned.

The present invention relates to fungicidal dispersions of 2-benzimidazole methylcarbamate (BCM) of the formula

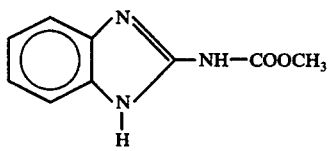

It is known from British Patent Spec. No.: 1,190,614 that BCM has excellent properties as a systemic plant fungicide. Because of its complete insolutility in lipoids, however, it does not penetrate easily through the plant surface into the interior of the plant where it can display its systemic activity. As a consequence, much of the material remains on the outer plant surface where it acts as a prophylactic fungicide only and is subject to the deteriorating influence of the weather.

The British patent describes a number of ways by which the penetrating capacity of BCM and hence its systemic activity may be improved, such as grinding it to a very fine particle size (below 5 microns) or adding larger-than-usual amounts of so-called "penetrants", i.e. compounds that facilitate the penetration of BCM into the plant interior. However, while these measures remove the drawbacks described above, they create others. For instance, dry milling to a very fine particle size requires special types of mills and expensive filtering apparatus, and the addition of large amounts of penetrants may cause toxicity hazards in the treated plants. Especially, it has not been possible to produce useful dispersions of BCM by the ways described in the British patent.

Such dispersions have a number of advantages over usual formulations such as dusts and wettable powders. Since for making dispersions the active compounds are ground in the wet state as slurries they do not require expensive filtering devices. Furthermore, dispersions are more easily dosable and do not dust while handling, thus reducing the hazards of toxicity to humans.

The preparation of stable dispersions is difficult. In order to prevent premature sedimentation the active compounds have to be ground very finely. In this state, however, strong Van der Waal's attraction forces appear between the dispersed particles causing aggregation and flocculation of the particles. To prevent this a surface active agent is usually added which concentrates at the solid-liquid interface and forms a solvating envelope around the individual particles carrying uniform electric charges and thus preventing agglomeration. Even so, however, the solvating envelope may break down partially e.g. if the dispersion is kept at higher temperatures over prolonged periods of time, which results in increasing viscosity, flocculation and irreversible sedimentation.

It is an object of the present invention to provide stable dispersions of BCM.

It is a further object of the invention to provide dispersions of BCM which have an improved systemic fungicidal activity as compared with previously described BCM-formulations and which are equal to the most active standard plant fungicides such as Benomyl (1-n-butylcarbamoyl-2-methoxy-carbonyl-amino-benzimidazol).

The fungicidal dispersions of the invention are characterized by a content of (a) about 5 to 30% by weight of 2-benzimidazole-methylcarbamate

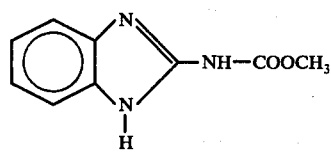

(b) about 60 to 85% by weight of liquid esters of ($C_1 - C_{12}$) monoalcohols and ($C_2 - C_{10}$) carboxylic acids, the esters containing at least 8 and, in the case of esters of monobasic acids, a maximum of 12 and, in the case of esters of dibasic acids, a maximum of 32 carbon atoms.

(c) about 2 to 10% by weight of a combination of a ($C_8 - C_{12}$)-monoalkylphenol polyglycol ether and castor oil polyglycol ether and (d) about 0.1 to 5% by weight of Ca-($C_8 - C_{15}$)-monoalkylbenzene sulfonate.

Within these limits the components and percentages may be varied to a large degree. It will be appreciated however that, if high percentages of active ingredient are desired, esters of low viscosity among those as claimed are used in order to ensure easy mobility of the dispersion obtained. Conversely, with smaller percentages of active ingredient esters of higher viscosity may be used.

Suitable esters are for example those of aliphatic ($C_6-C_{10}$)-carboxylic acids such as caproic, capric, caprylic and perlargonic acid or esters of aromatic carboxylic acids such as benzoic, toluic, salicylic and phthalic acid. Suitable alcohol components of these esters are, for example, butanol, n-octanol, i-octanol, dodecanol, cyclopentanol, cyclohexanol, cyclooctanol or benzyl alcohol. Examples of suitable esters are benzyl acetate, caproic acid ethyl ester, perlargonic acid ethyl ester, benzoic acid methyl or ethyl ester, salicylic acid methyl, propyl or butyl ester. Especially preferred are diesters of phthalic acid with aliphatic or alicyclic ($C_1-C_{12}$)-alcohols, such as phthalic acid dimethyl ester, dibutyl ester, diisooctyl ester, didodecyl ester, dicyclopentyl ester, dicyclohexyl ester or dicyclooctyl ester.

The combination of monoalkylphenol polyglycol ether and castor oil polyglycol ether acts as surface active agent in the composition according to the invention.

Suitable monoalkylphenol polyglycol ethers are especially those having 8 to 9 carbon atoms in the alkyl moiety and a variable degree of ethoxylation, preferably 5 to 14 ethylene oxide (AeO) units and, especially 8 to 12 AeO units. Examples of such compounds are the types commercially available under the trade name "Triton ®", for example Triton X-45, X-114 and X-207. Their proportion in the total formulation is advantageously from 3 to 4% by weight. The castor oil polyglycol ethers which are also required have a degree of ethoxylation preferably in the range of from 30 to 50 and especially of from 36 to 40 AeO units. They are for instance commercially available under the trade name "Emulsogen EL®", their proportion is advantageously in the range of from 1.5 to 3% by weight. The calcium salts of higher monoalkyl benzene sulfonic acids may be used as additives to the dispersions owing to their solubility in organic solvents. Calcium salts of ($C_{10}$-$C_{12}$)-monoalkyl benzene sulfonic acids, especially of dodecyl benzene sulfonic acid, are preferably used. Their content is preferably 0.5 to 5%, especially 2 to 4% by weight.

The Ca-alkylbenzene sulfonates may be added in the solid state or, preferably, in alcoholic solution, for example in isopropanol or isobutanol.

The dispersions of the invention are prepared in known manner, for example by grinding the starting material in ball mills by means of quartz pearls having a diameter of from 1 to 2 mm. The active ingredient in the dispersions obtained has a particle size of less than 10, preferably of less than 5 microns.

The composition of the emulsifier is critical for the properties of the formulation. Comparative tests have shown that commonly used emulsifiers such as polyglycol esters of oleic acid, stearic acid or palmitic acid, polyglycol derivatives of dodecylmercaptan, of oleylamines or stearylamines do not form storable dispersions with BCM. The same applies to polyglycol ethers of oleyl, stearyl and technical coconut fat alcohols and of dodecylalcohol, of varying degrees of polymerization. Alkylphenol polyglycol ethers used alone were likewise unsuitable.

The dispersions according to the invention on the other hand are distinguished by an excellent activity and a high storability. In this respect they are considerably superior to the dispersions known from British Patent Specification No. 1,190,614 (example 5). Their efficiency is also superior to known wettable powder formulations of BCM and to Benomyl formulations, as the following examples illustrate.

EXAMPLE 1 (Comparative agent 1)

According to example 5 of British Patent Specification No. 1,190,614 a dispersion was prepared containing 26% by weight of BCM 38.57% by weight of indene resin (Piccolyte resin S-10)

26.43% by weight of low boiling isoparaffin oil (Soltrol 130®)

9% by weight of lauryl alcohol polyglycol ether.

115.71 g (38.57%) of Piccolyte resin S-10 were dissolved in 79.29 g (26.43%) of Soltrol 130 and introduced into the stirring compartment of a ball mill. Then 78 g (26%) of BCM, 27 g (9%) of laurylalcohol polyglycol ether having a polymerization degree of 10 and 500 g of 1 mm quartz pearls were added and the whole was ground for 6 hours. Thereafter the BCM had a particle size of less than 5 microns. The quartz pearls were then separated by sieving.

After a storage life of 3 months the dispersion was viscous, the sediment could not be redispersed in the container and dispersed in water only with great difficulty.

EXAMPLE 2

A BCM dispersion according to the invention and containing 20.00% by weight of BCM 4.00% by weight of Ca-dodecylbenzene sulfonate (in the form of a 70% solution in i-butanol)

2.66% by weight of castor oil polyglycol ether ("Emulsogen EL 400®")

3.34% by weight of octylphenol polyglycol ether ("Triton X-207®")

70.00% by weight of phthalic acid diisooctyl ester ("Genomoll 100®") was prepared in the same manner.

EXAMPLE 3

Another dispersion had the following contents:

15% by weight of BCM

3% by weight of Ca-dodecylbenzene sulfonate 2.7% by weight of castor oil polyglycol ether 3.3% by weight of octyphenol polyglycol ether (Triton X-207)

76% by weight of phthalic acid diisononyl ester (Genomoll 150)

EXAMPLE 4

Another dispersion had the following contents:

25% by weight of BCM 4.2% by weight of Ca-dodecylbenzene 2.48% by weight of castor oil polyglycol ether (Emulsogen EL 400®)

2.00% by weight of octylphenol polyglycol ether (Triton X-207®)

1.32% by weight of octylphenol polyglycol ether (Triton X-117®)

65% by weight of phthalic acid diisobutylester (Genomoll 140®)

A commercial Benomyl powder was used as a further comparative agent (comparative agent 3).

EXAMPLE 5

Cucumber plants were cut off above the first two true leaves. As soon as these were completely grown, the cotelydons situated below were also removed and the lower parts of the leaves were sprayed to the drip off with aqueous preparations of the composition of example 2 by means of a microapplicator.

Care was taken to insure that the upper surface of the leaves and other parts of the plant as well as the soil were not contaminated by active ingredient.

The comparative preparation of example 1 was used as comparative agent.

The compositions of the test preparations and of the comparative agents were applied in concentrations of 1000, 500, 250, 125, 60 and 30 mg each of active ingredient per liter of spraying liquid.

After drying, the upper surface of the leaves was infected with conidia of cucumber mildew (Erysiphe cichoracearum). The plants were then placed in a green house at a relative humidity of 80 to 90% and a temperature of from 23° to 25° C. After an incubation time of 14 days the plants were examined visually as to the degree of damage by cucumber mildew. The degree of damage was expressed in percent of attacked surface of the leaves compared to infected untreated controls.

From the result indicated in table 1 it is seen that the activity of the dispersion prepared according to British Patent Specification No. 1,190,614 was considerably lower than that of the dispersion according to the invention. The latter dispersion was also by far superior to the commercial formulation of Benomyl.

EXAMPLE 6

Apple seedlings in the 8-leaf-state were defoliated, except for the 4 youngest unfilded leaves, strongly infected with conidia of apple scab (*Venturia inaequalis*)

and placed dripping wet in a climatic chamber having a relative humidity of 100% and a temperature of 20° C.

After 2 days the plants were put in a green-house adjusted to a temperature of 18° C and a relative humidity of 90 to 95%.

After 3 days the lower surfaces of the leaves were sprayed to the drip off with aqueous preparations of the dispersions prepared according to example 2 using the same precautions as in Example 3.

A dispersion prepared according to example 1 (comparative agent 1) and a dispersion of Benomyl (comparative agent 2) were applied as comparative agents in an analogous manner. The applied concentrations were 1000, 500, 250, 60 and 30 mg each of active ingredient per liter of spraying liquid.

After drying the plants were replaced in the greenhouse and examined visually as to the degree of damage by apple scap after an incubation time of 21 days. The degree of damage was expressed in percent of attacked surface of the leaves calculated on infected untreated controls.

From the test result indicated in table 2 it is seen that the activity of the formulation according to the invention was considerably higher than that of the comparative agent 1.

The formulation according to the invention was also superior to the comparative agent 2.

TABLE 1

| Composition of the Substance | % of surface of the leaves infected by cucumber mildew mg of active ingredient per liter of spraying liquor | | | | | |
|---|---|---|---|---|---|---|
| | 1000 | 500 | 250 | 125 | 60 | 30 |
| 20 % BCM-dispersion according to example 2 Comparative agent 1 | 0 | 0 | 0 | 0 | 6 | 12 |
| BCM-dispersion according to British Patent Specification No. 1,190,614 Example 1 Comparative agent 2 | 0* | 15* | 30 | 65 | 85 | 100 |
| Commercial wettable powder of Benomyl | 0 | 0 | 0 | 8 | 15 | 32 |
| Non-treated infected control plant | 100 | 100 | 100 | 100 | 100 | 100 |

*marked damages of the leaves

TABLE 2

| Composition of the Substance | % of surface of the leaves infected by apple scap mg of active ingredient per liter of spraying liquor | | | | | |
|---|---|---|---|---|---|---|
| | 1000 | 500 | 250 | 125 | 60 | 30 |
| 20 % BCM-dispersion according to example 2 Comparative agent 1 | 0 | 0 | 0 | 0 | 2 | 10 |
| BCM-dispersion according to British Patent Specification No. 1,190,614 Example 1 Comparative agent 2 | 0* | 3* | 10 | 20 | 42 | 58 |
| Commercial wettable powder of Benomyl | 0 | 0 | 0 | 8 | 15 | 27 |
| Non-treated infected control plant | 100 | 100 | 100 | 100 | 100 | 100 |

*marked damages by burning of the leaves

What is claimed is:

1. A fungicidally active composition of
   (a) about 5 to 30 percent by weight of the compound of the formula

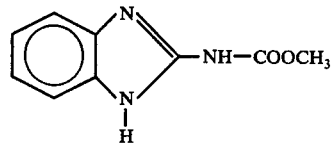

(b) dispersed in about 60 to 85 percent by weight of a liquid diester of an aliphatic or alicyclic ($C_1$–$C_{12}$) monoalcohol and phthalic acid,
   (c) about 2 to 10 percent by weight of a combination of octylphenol polyglycol ether and castor oil polyglycol ether, said octylphenol polyglycol ether having from 5 to 14 glycol units and said castor oil polyglycol ether comprising 1.5 to 3 percent by weight of said combination and having from 30 to 50 glycol units and
   (d) about 0.1 to 5 percent by weight of Ca-($C_8$–$C_{15}$)-monoalkyl benzene sulfonate.

2. The composition of claim 1 wherein the liquid ester is phthalic acid diisooctyl ester.

* * * * *